(12) United States Patent
Reynolds et al.

(10) Patent No.: US 8,368,891 B2
(45) Date of Patent: Feb. 5, 2013

(54) DEVICE AND PROCESS TO MEASURE WATER CLARITY AND ORGANIC CONTENT

(76) Inventors: William Thomas Reynolds, Pasadena, CA (US); Burton Harold Jones, Pasadena, CA (US)

(*) Notice: Subject to any disclaimer, the term of this patent is extended or adjusted under 35 U.S.C. 154(b) by 200 days.

(21) Appl. No.: 12/774,258

(22) Filed: May 5, 2010

(65) Prior Publication Data

US 2010/0309471 A1 Dec. 9, 2010

Related U.S. Application Data

(60) Provisional application No. 61/184,991, filed on Jun. 8, 2009.

(51) Int. Cl.
G01N 21/85 (2006.01)
G01N 21/25 (2006.01)
(52) U.S. Cl. ........................ 356/419; 356/411
(58) Field of Classification Search .......... 356/411, 356/419
See application file for complete search history.

(56) References Cited

U.S. PATENT DOCUMENTS 7,746,452 B2 * 6/2010 Fuchigami et al. ............ 356/73
2004/0233447 A1 * 11/2004 White et al. .................. 356/417

OTHER PUBLICATIONS

Bonaire National Park—Light and Motion, May 9, 2008, http://web.archive.org/web/20080509083243/http://www.bmp.org/lightandmotion.html.*
Morel, André, et al., Optical Properties of the "clearest" natural waters, 2007, American Society of Limnology and Oceanography, Inc., Limnol. Oceanogr., 52(1), 217-229.*

* cited by examiner

Primary Examiner — Gregory J Toatley
Assistant Examiner — Dominic J. Bologna

(57) ABSTRACT

A method of using a sensor array that measures the long-term change in the organic content of the near-surface seawater by simultaneously comparing downwelling sunlight attenuation in the blue and green wavelengths over a significant vertical distance.

1 Claim, 3 Drawing Sheets

DEVICE AND PROCESS TO MEASURE WATER CLARITY AND ORGANIC CONTENT

RELATED APPLICATIONS

The present application claims benefit of priority from U.S. Provisional Application No. 61/184,991, filed Jun. 8, 2009, which is incorporated herein by reference in its entirety.

BACKGROUND OF THE INVENTION

The present invention generally relates to a device and process to measure water clarity and organic content.

The typical method of measuring chromophoric dissolved organic material (CDOM) and chlorophyll, the normal organic components of seawater, is with a fluorometer. A fluorometer has a carefully controlled light source that emits light at a specific wavelength and a detecting mechanism that measures emitted light in a different (longer) wavelength. To measure CDOM, the medium is excited in the ultraviolet wavelength and the reemitted (fluoresced) light is detected in the blue range. For chlorophyll, the sample is excited in the blue wavelength and the reemitted light detected in the red wavelength.

Fluorometers measure only a very small sample volume and require very expensive instrumentation to create an accurate excitation beam and a similarly accurate detection mechanism. Electrical power is required for the light excitation source in a fluorometer, the result being an apparatus costing upwards of $25,000 USD to measure CDOM and chlorophyll.

As can be seen, there is a need for an economical device to measure water clarity and organic content.

SUMMARY OF THE INVENTION

In one aspect of the present invention, a sensor array is described comprising a first blue sensor and a second blue sensor; and a first green sensor and a second green sensor; wherein the blue sensors have a filter that only passes blue light, and the green sensors have a filter that only passes green light.

In another aspect of the present invention, a method to calculate an index of the organic content of water is described comprising measuring the attenuation characteristics of downwelling sunlight in the blue and green wavelengths of the color spectrum at two different distances from the surface of the water; and calculating the index of the organic content.

In yet another aspect of the present invention, a sensor array system for measuring an index of the organic content of water is described comprising a mooring line attached at a first end to a mooring anchor and attached at a second end to a float; and two light sensor sets, each set having a blue sensor and a green sensor; wherein the light sensor sets are attached to the mooring line and the light sensor sets are spaced along the mooring line.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, an embodiment of the present invention generally provides an economical process and apparatus to measure water clarity, visibility and the organic content of seawater. The apparatus can be deployed in-ocean for extended periods.

Figure 1:
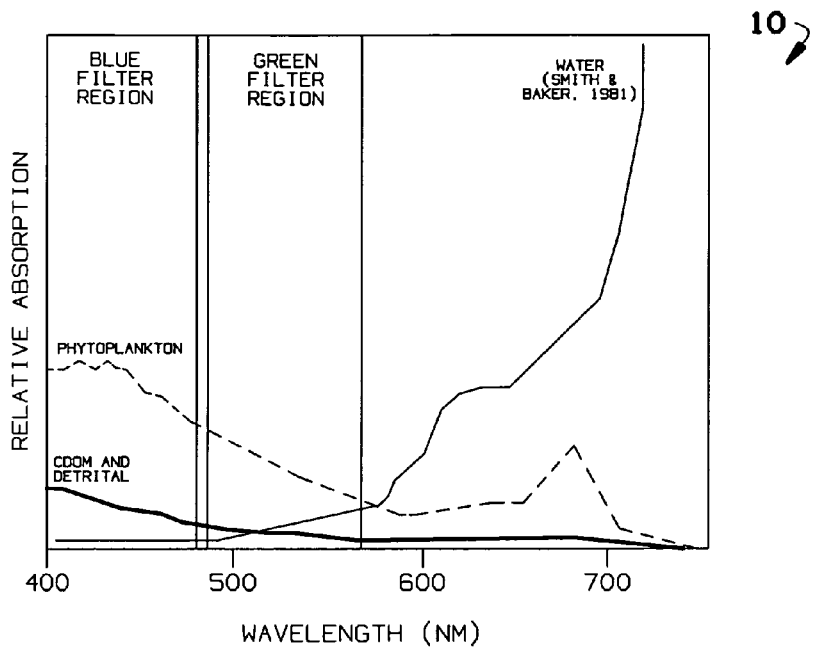
FIG. 1 is a graph of an exemplary embodiment of the absorption spectrum for water, phytoplankton, and chromophoric dissolved organic material (CDOM) and particulate organic material (detritus) in the wavelengths used by the Rainbow Sensor®, with the X-axis showing the light spectrum and the Y-axis showing relative absorption of light in the water.

As light passes through seawater, the intensity of light declines as the depth increases, because water attenuates light. Different colors attenuate at different rates. Further, in addition to the water itself, particles and dissolved matter in the water increase the attenuation of the light at specific wavelengths (FIG. 1). The data in FIG. 1 are taken from Smith and Baker (Smith, R. C. and K. S. Baker (1981). "Optical-Properties of the Clearest Natural-Waters (200-800 Nm)." *Applied Optics* 20(2): 177-184).

Figure 2:
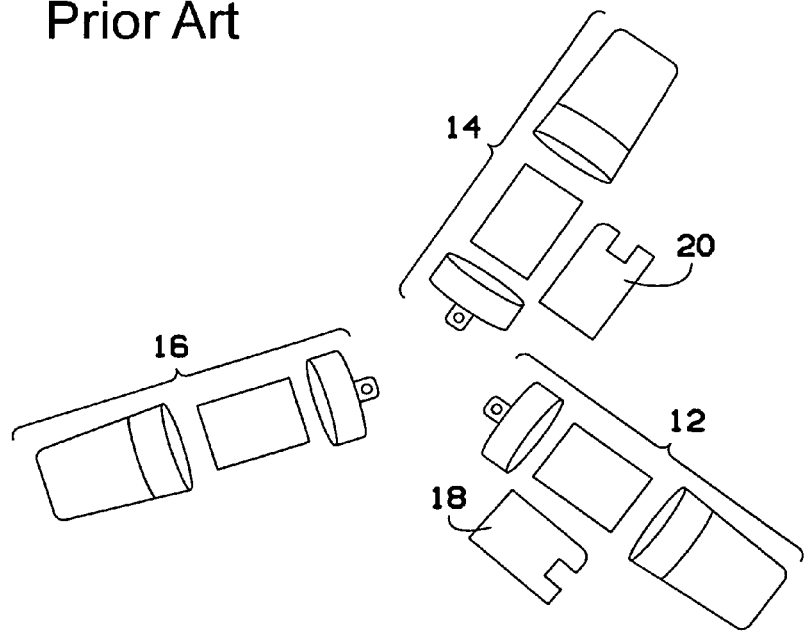
FIG. 2 depicts an exploded view of an exemplary embodiment of one set of the blue, green and white sensors according to the invention.
Figure 3A:
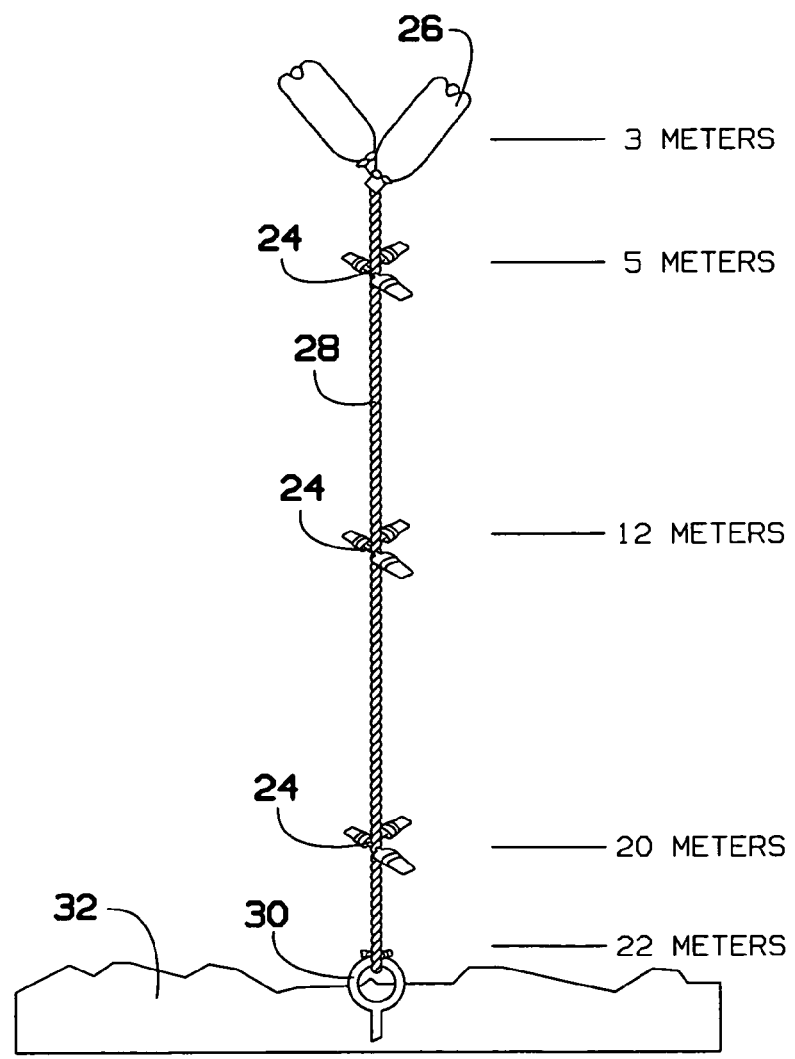
FIG. 3A depicts an exemplary embodiment of a mooring configuration using three sets of sensors according to the invention.

An exemplary embodiment of the Rainbow Sensor® array can be an array of three sets of sensors 24 deployed in the water (FIG. 3A). In one embodiment, commercially available HOBO® Pendant sensors 16 (Onset Computer, Bourne, Mass.) can be modified with optical filters to create the components of the Rainbow Sensor® array (FIG. 2). Other appropriate sensors can also be used.

Another exemplary embodiment of the array can include two sensor sets, such that the array comprises a blue sensor 14 pair, a green sensor 12 pair and, optionally, a white (unmodified) sensor 16 pair. The color filters 20, 18 of the blue 14 and green 12 sensors on the Rainbow Sensor® array can enable the measurement of attenuation of specified light wavelengths as the light passes through the water. Each blue pair and each green pair works in conjunction. The sensors at 12 meters measure blue and green wavelengths at that depth while the sensors at 20 meters measure blue and green at 20 meters depth. In the 8 meters between 12 meters depth and 20 meters depth the light has attenuated. The difference between the light levels at 12 meters 20 and 20 meters is the attenuation that has occurred in 8 meter water column between the sensors. Custom software can use the light measurements from these customized sensors to calculate the index of organic content of seawater.

Unmodified HOBO® Pendant sensors measure white light that spans the visible light spectrum. In the instant device, the sensor 16 can be modified by insertion of a special filter 18, 20 that may allow light of only a limited range of wavelengths (color) to pass through. For example, in one embodiment, commercially available filters Green Lee Filter #124 and Blue Lee Filter #798 can be used (Lee Filters, Burbank, Calif.). The third sensor 16 can be unmodified and thus pass all wavelengths (white light) and can be used as a reference.

Figure 3B:
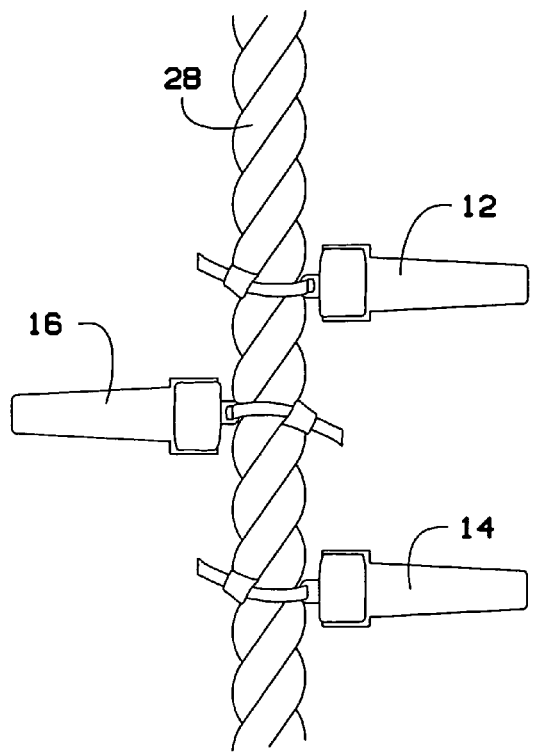
FIG. 3B depicts a side view of an exemplary embodiment of one set of the blue, green and white sensors according to the invention.
Figure 3C:
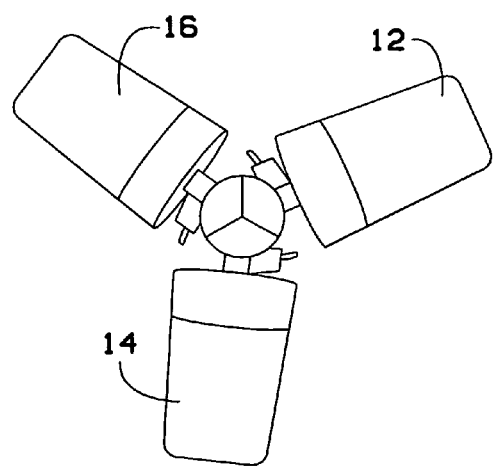
FIG. 3C depicts a cut-away top view of an exemplary embodiment of one set of the blue, green and white sensors according to the invention.

In an exemplary embodiment, blue 14, green 12, and white 16 sensor sets 24 (FIGS. 3B and 3C) can be placed on an underwater sea mooring (FIG. 3A) comprising a half-inch polypropylene rope mooring line 28, moored to the ocean floor 32 by attaching to a mooring anchor 30 and utilizing a buoyancy system 26 to suspend the mooring line 28. The sensor sets 24 can be placed at two different depths, for example 12 meters and 20 meters. The mooring anchor 30 can be set into the ocean floor 32 at a depth below the deepest sensor set 24; in this example the mooring anchor 30 can be set at 22 meters. Optionally, a third sensor set 24 may be placed at 5 meters. Other depths can be used as appropriate depending upon light levels and water clarity. These sensors 24 can record results continuously. The sensors are programmed to measure temperature and light continuously at one minute intervals. Divers use an underwater optical reader to download data and re-launch the sensors on each mooring weekly. The sensor data can be retrieved, for example using a HOBO® Waterproof Shuttle that can transfer the data, underwater from the HOBO® Pendant sensors to the HOBO® Waterproof Shuttle, and can be input into custom software, which can calculate an index of the organic content of water. This result can be called the "Organic Index".

To calculate the Organic Index, sensor pairs (i.e. blue and blue or green and green) can work together. For example, the sensor set 24 at 12 meters can measure the intensity of blue and green wavelengths at that depth, while the sensor set 24 at 20 meters can measure intensity of blue and green wavelengths at 20 meters depth. In the 8 meters between the 12-meter depth and the 20-meter depth, the light has attenuated. The difference between the light intensity at 12 meters and 20 meters is the attenuation that has occurred in the 8-meter water column between the sensors. The reduction in light intensity of a specific wavelength between the sensor of a specific color at 12 meters and the sensor of the same color at 20 meters depth is the attenuation of that wavelength over the 8-meter span. Using a calculation (formula below), the light measurements can be converted to numbers (attenuation coefficients) that can be called "$K_{Ed}$(blue)12-20" and "$K_{Ed}$(green) 12-20".

Organic components, such as dissolved organic material and chlorophyll contained in phytoplankton, together with other suspended particles, may strongly affect $K_{Ed}$(blue) over a particular depth range by absorbing blue light. Therefore, water clarity can be affected both by the presence of organic material and inorganic particles. However, in the green range, light attenuation (increased $K_{Ed}$(green) is generally much less affected by organic material, but it is most affected by suspended particles. Therefore, if the blue attenuation ($K_{Ed}$(blue)) over a particular depth range increases at a greater rate than green attenuation ($K_{Ed}$(green)) over the same depth range, the difference can be due to the absorption of blue light by organic material in the water.

These measurements can be used to calculate the Organic Index. An increase of $K_{Ed}$(blue) over a particular depth range relative to $K_{Ed}$(green) over the same depth range can mean increased organic content and increased Organic Index. The Organic Index can be calculated as follows: For each depth pair, the diffuse downwelling attenuation coefficient ($K_{Ed}(\lambda)$) is calculated from the downwelling irradiance for each color region using equation 1:

$$K_{Ed}(\lambda) = -\frac{\ln\left(\frac{E_d(\lambda, z_2)}{E_d(\lambda, z_1)}\right)}{z_2 - z_1}$$

$E_d(\lambda,z)$=downwelling (downward propagating) irradiance at wavelength λ at depth z
$K_{Ed}(\lambda)$=diffuse downwelling light attenuation coefficient for wavelength lambda.

In an exemplary embodiment of the Rainbow Sensor® array, three $K_{Ed}$'s can be calculated between the blue 14, green 12 and white 16 sensor pairs for the depth interval 8 meters, between the 12-meter and the 20-meter sensor sets 24. The data can be exported from the HOBO® Waterproof Shuttle using a proprietary package from the HOBO® Sensor manufacturer (HoboWare® Pro from Onset Computer Corporation) into a formula readable by an engineering analysis application (for example, MATLAB® from The MathWorks, Inc.). The engineering analysis software can assemble the data in a time series for each sensor and create an array based on the configuration of the Rainbow Sensor® array. The software can then calculate the $K_{Ed}$(blue), $K_{Ed}$(green) and OI based on the formula described above. Data smoothing techniques can be used to reduce the data noise before calculating each K and the OI. In one instance, a simple daily mean for the four hours surrounding solar noon can be used for a single daily $K_{Ed}$(blue) and $K_{Ed}$(green) determination.

$K_{Ed}$(blue) can provide a measure of water clarity. Lower $K_{Ed}$(blue) values over a particular depth range can indicate higher water clarity, and higher $K_{Ed}$(blue) values over a particular depth range can indicate lower clarity. Clarity is somewhat different from visibility. Visibility can be affected by many factors, including the amount of sunlight on the water. A calculation using the $K_{Ed}$(blue) and the total white light at 20 meters can be used to determine visibility.

Visibility is inversely proportional to clarity ($K_{Ed}$(blue)12-20) and reduced by the amount of ambient light (Par_20). Visibility=f(a){1/$K_{Ed}$(blue) (12-20)}*{f(b)(Par_20)} where f(a) and f(b) are functions derived from comparing Rainbow Sensor® readings with other scientific measurements.

The Rainbow Sensor® array can use available light such as sunlight (which is an unmodulated source), and measure the same wavelengths at different depths from the source to measure light attenuation in that wavelength. Whereas the fluorescence at certain wavelengths is directly proportional to organic content, attenuation is the combination of light absorption and scattering. Therefore the Rainbow Sensor® array can use the difference in attenuation of two wavelengths to calculate organic content.

The Rainbow Sensor® approach can be cost effective. It does not require a highly modulated light source and the associated battery power source, thus creating a less complicated measurement device for in-ocean organic content of seawater. In addition, the Rainbow Sensor® array can use a sample length of meters, rather than centimeters, yielding an average reading over a longer depth range and increase sensitivity.

An exemplary embodiment of the instant device and method, the Light and Motion Sensor Program (LMSP) in Bonaire, Dutch Caribbean, can illustrate the benefits of the Rainbow Sensor® array. The LSMP in Bonaire uses the Rainbow Sensor® array to measure $K_{Ed}$ for blue, green and broadband white light from sensors at three depths. The program uses HOBO® Pendant temperature/light sensors (Onset Computer, Bourne, Mass.) with transparent colored filters inserted in two of the sensors. The three sensor sets 24 were placed in an array at a specific depth below the surface (FIG. 3A). On the LMSP moorings sensor sets were placed at 5 meter, 12 meter and 20 meter depths, for a total of nine sensors per mooring (see FIG. 3A). The sensors were placed face up so that they are measuring the downwelling irradiance, $E_d$, at each depth for each spectral range.

The Rainbow Sensor® array demonstrated that it can detect events in both temperature and in the diffuse attenuation coefficient in the blue portion of the spectrum. Two patterns in blue absorption were observed. One was a response to regional coastal upwelling off of Venezuela that could be seen in the remote sensing imagery to advect cool, chlorophyll enriched water toward Bonaire. The second pattern was a seasonal pattern where higher values of $K_{Ed}$(blue) were observed during winter months than during spring/early summer. In this program, fourteen Rainbow Sensor® arrays were deployed. The total cost of all 14 arrays was $20,000 USD.

The Rainbow Sensor® concept can provide a reasonable measure of $K_{Ed}$ in the blue portion of the spectrum. Because most of the variability between 400 and 490 nm is associated with organic matter in various forms including CDOM, chlorophyll and particulate organic material, variability of $K_{ed}$ in this region of the spectrum can represent changes in the organic content of the water column. The Rainbow Sensor® array can be an effective, inexpensive approach to monitoring changes from contamination that might affect the reef ecosystem. Because it records its data at a reasonably high frequency, it can provide the ability to resolve processes over a range of time scales range from minutes to years, depending on the lifetime of the moorings.

It should be understood, of course, that the foregoing relates to exemplary embodiments of the invention and that modifications may be made without departing from the spirit and scope of the invention as set forth in the following claims.

We claim:

1. A method to calculate an index of an organic content of water comprising:
    measuring an attenuation of downwelling sunlight in a blue wavelength and in a green wavelength wherein
        measurements are taken at a first point at a first depth and a second point at a second depth,
        the first depth and the second depth are separated by a vertical distance of greater than 8 meters,
        the first depth and the second depth are each at a distance of between 5 meters and 20 meters below a surface of water,
        the measurements at the first depth and the second depth are taken at essentially the same time, and
        the measurements at the first point and the second point are performed in a vertical column;
    calculating a comparison of the attenuation of downwelling sunlight in the blue wavelength and the green wavelength between the measurement taken at the first depth and the second depth, in the same vertical water column, and at essentially the same time;
    wherein measurements are taken
        every minute, and
        for a period of time greater than a year; and
    wherein the measurements comprise data obtained by a waterproof temperature and light data logger, connected to a mooring line attached to a seabed.

* * * * *